United States Patent [19]

Montgomery et al.

[11] 3,965,206

[45] June 22, 1976

[54] PRODUCTION OF STILBENE AND STYRENE

[75] Inventors: Phillip D. Montgomery, Creve Coeur; Richard N. Moore, St. Louis; Walter R. Knox, Town and Country, all of Mo.

[73] Assignee: Monsanto Company, St. Louis, Mo.

[22] Filed: Dec. 5, 1974

[21] Appl. No.: 529,985

Related U.S. Application Data

[63] Continuation-in-part of Ser. No. 430,018, Jan. 2, 1974, abandoned.

[52] U.S. Cl. .................... 260/669 R; 260/668 D; 260/674 R; 260/674 SA
[51] Int. Cl.² .................. C07C 15/10; C07C 15/187
[58] Field of Search ........ 270/669 R, 668 D, 680 R, 270/669 B

[56] References Cited

UNITED STATES PATENTS

| | | | |
|---|---|---|---|
| 2,674,636 | 4/1954 | Zar et al. | 260/674 |
| 3,476,747 | 11/1969 | Hargis et al. | 260/669 R |
| 3,494,956 | 2/1970 | Greene et al. | 260/680 R |
| 3,526,676 | 9/1970 | Turner et al. | 260/683.2 |
| 3,761,536 | 9/1973 | Bozik et al. | 260/680 R |

*Primary Examiner*—D. Horwitz
*Attorney, Agent, or Firm*—Elizabeth F. Sporar; Paul L. Passley

[57] ABSTRACT

Toluene and toluene derivatives are dehydrocoupled to stilbene and stilbene derivatives in a vapor phase reaction in the presence of a metal oxide. The stilbene products are purified of by-product polar impurities. The purified stilbene can be catalytically reacted in the vapor phase with ethylene to produce styrene.

23 Claims, No Drawings

PRODUCTION OF STILBENE AND STYRENE

BACKGROUND OF THE INVENTION

This application is a continuation-in-part of application Ser. No. 430,018 filed Jan. 2, 1974, and now abandoned.

This invention relates to the manufacture and purification of 1, 2-diphenylethylene (stilbene) and derivatives thereof. In a further aspect of this invention relates to the manufacture of styrene from the purified stilbene obtained in accordance with this invention.

Stilbene, because of its unsaturated character, is very reactive and may be employed in various organic syntheses. Derivatives of stilbene are useful in the production of products which may be used in the manufacture of dyes, paints and resins. It is also useful in optical brighteners, in pharmaceuticals and as an organic intermediate.

Stilbene has been synthesized by dehydrogenation of bibenzyl; by dehydrogenation of 1, 2-bis(3-cyclohexen-1-yl) ethylene (U.S. Pat. No. 3,387,050); and by reacting a benzyl mercaptan with a sulfactive catalyst, for example, molybdenum disulfide and copper-sulfide (U.S. Pat. No. 2,645,671). Stilbene and halostilbenes have been synthesized by the iodative dehydrocoupling of toluene and halogen-substituted toluenes with elemental iodine and molten lithium iodide at toluene conversions of 10–30% (U.S. Pat. No. 3,409,680).

Dehydrocoupling of toluene by the reaction with lead oxide to form stilbene has been reported by Behr and Van Dorp, Chem. Ber. 6,753 (1873) and Lorenz, Chem. Ber. 7,1096 (1874). In this reported work, stilbene is obtained by conveying toluene over lead oxide maintained at or about at a dark red glow. A more recent disclosure of the toluene lead oxide reaction is given in U.S. Pat. No. 3,494,956. In Example 9 of this patent, it is reported that a mixture of toluene and oxygen passed over heated lead oxide produces bibenzyl. In U.S. Pat. No. 3,557,235 it is reported that toluene can be oxidatively coupled in a stoichiometric reaction where a metal oxide, such as lead oxide, serves as the source of oxygen in the reaction.

Styrene is currently commercially produced from benzene in a two-step process. In the first step benzene is alkylated with ethylene to form ethylbenzene, and in the second step, the ethylbenzene is dehydrogenated to form styrene. Toluene is less expensive than benzene and thus a commercially feasible process for producing styrene from toluene would be desirable.

In Netherlands Patent Application No. 66-18110, it is disclosed that ethylene will react in the presence of a disproportionation catalyst with alkenes having at least 4 carbon atoms and without double bonds at the ends to form 1-alkenes having a number of carbon atoms intermediate of the alkenes reacted Stilbene (1, 2-diphenylethylene) is an example of a reactant alkene. Similarly, U.S. Pat. No. 3,526,676, discloses the formation of 1-olefins from internal (other than 1-position) olefins by reaction with ethylene in the presence of an olefin disproportionation catalyst.

SUMMARY OF THE INVENTION

This invention is directed in a broad aspect to the manufacture of stilbene from toluene and to the purification of the stilbene to remove by-product organic and inorganic polar impurities. A further aspect of this invention is directed to the manufacture of styrene from the purified stilbene obtained in accordance with the broad aspect of this invention and ethylene.

Accordingly, typical objects of this invention are to provide: (1) a process of producing stilbene using toluene as the only raw material hydrocarbon, (2) a process for producing and recovering stilbene free of organic and inorganic polar impurities, (3) a process for producing styrene using toluene and ethylene as raw material hydrocarbons, and (4) a process capable of producing two moles of styrene from two moles of toluene and one mole of ethylene.

Other objects, aspects and advantages of this invention will hereafter become apparent.

In accordance with this invention, speaking on a molar basis, two moles of toluene are oxidatively dehydrocoupled in a vapor phase reaction carried out under heat and in the presence of only lead oxide to form one mole of stilbene. A stilbene fraction is recovered from the reaction effluent containing unreacted toluene and by-products is treated to remove organic and inorganic polar impurities. By "organic and inorganic polar impurities," hereinafter referred to for brevity's sake as "polar impurities," are meant in relation to the present invention, oxygenated compounds, for example, ketones such as benzophenone (diphenyl ketone), 2-methylbenzophenone, 4-methylbenzophenone, 9-fluorenone, anthraquinone and the like, aldehydes such as benzaldehyde, and alcohols such as benzyl alcohol, phenol and the like and water. In accordance with a further aspect of the invention one mole of the purified stilbene and one mole of ethylene are catalytically reversibly disproportionated in a vapor-phase reaction carried out under heat and in the presence of a disproportionation catalyst to form two moles of styrene.

The broad aspect of this invention may be represented by the following equation:

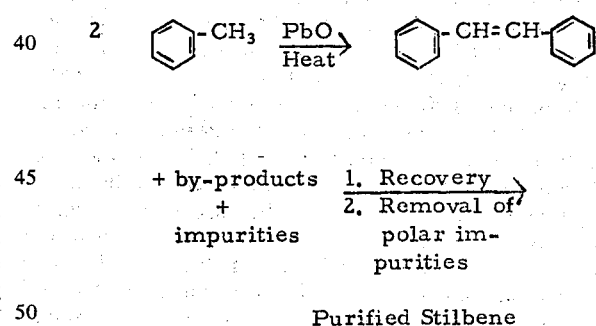

Purified Stilbene

The total reaction of this invention may be represented by the following equation:

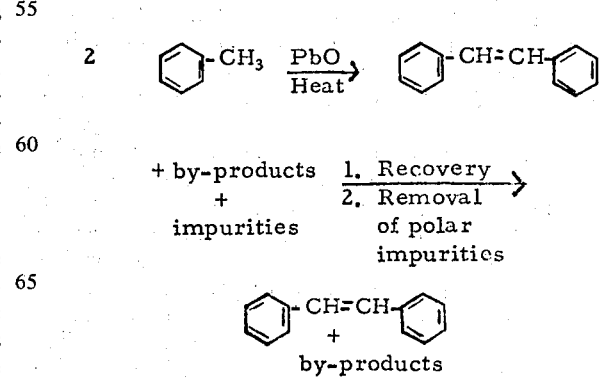

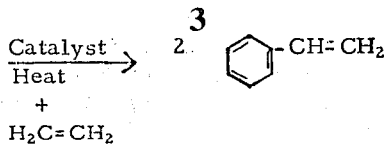

As previously indicated the oxidative dehydrocoupling reaction is carried out in the vapor phase and under the influence of heat. The temperature range under which the reaction can be carried out extends from about 500°C to about 650°C, preferably, 540°C to 600°C. The reactant toluene will generally be heated and introduced to the reactor as a vapor. However, the toluene may be introduced to the reactor as a liquid and then vaporized. The reaction is conducted in the presence of a metal oxide which effects partial dehydrogenation of the methyl group of the toluene and coupling of such dehydrogenated toluene to form stilbene. This reaction is conducted in the absence of added free oxygen and employs only that oxygen carried by the metal oxide. Any metal oxide capable of carrying and supplying the necessary stoichiometric quantity of oxygen and which is effective to dehydrocouple toluene under the reaction conditions can be employed. Suitable metal oxides are, for example, lead oxide, cadmium oxide and bismuth oxide. The metal oxides may be employed individually or as mixtures. They may be employed alone or with a support. Suitable supports, for example, are silica, alumina, silica-alumina, metal aluminates such as magnesium aluminate, and the like. The surface area of the support will generally be in the range of from about 0.1 to 10 m²/g. The reaction will suitably be conducted at a toluene conversion level of 2 to 100 percent.

If desired, the metal oxide can be formed in the reactor by placing the metal in the reactor and heating it until it becomes molten. Air or oxygen can then be passed through the molten metal to form the metal oxide as a solid which forms a layer on top of the molten metal. Toluene can then be passed through the layer of metal oxide to form stilbene in accordance with this invention.

The reaction effluent contains, in addition to stilbene (cis and trans) and unreacted toluene, by-products, such as benzene, bibenzyl, and polar impurities. A stilbene fraction contained in the reaction effluent is separated and purified for further use in the instant process. The separation of the stilbene fraction from the reaction effluent can be accomplished by known distillation techniques including azeotropic distillation. During such separation, other valuable materials, such as benzene, contained in the reaction effluent can be advantageously recovered and used. For example, the unreacted toluene as well as the bibenzyl and cis-stilbene can be recycled to the dehydrocoupling step.

The purification of the separated stilbene fraction to remove the polar impurities can be accomplished by a number of different methods. Such polar impurities adversely affect the catalyst used in the reverse disproportionation reaction. A satisfactory method of removing such polar impurities comprises passing the stilbene through a bed of solid material capable of selectively absorbing the polar impurities. Suitable solid materials are, for example, diatomaceous earth, alumina and the like. The absorption of the polar impurities from the stilbene is conducted in the liquid phase and at a temperature of from about 75°C to about 200°C, preferably from 125° to 150°C. The liquid stilbene is passed through the bed of absorbent at such a rate to provide a residence time of the stilbene in the bed of from about 0.1 second to 15 minutes. The stilbene can be recovered from the dehydrocoupling reaction effluent as a liquid or in crystalline form which is then melted. The stilbene can also be dissolved in benzene or toluene prior to being passed through the absorbent.

Another method for removal of polar impurities from the stilbene fraction involves treatment of the fraction with chemical reagents. Suitable treating agents are the alkali metals such as sodium, lithium, potassium and the like, organometallic compounds of the metals of Groups IA, IIA, and IIIA of the Periodic Table such as phenyllithium, disodium stilbene, alkyl aliminums such as triethylaluminum and triisobutylaluminum, aluminum alkoxides such as aluminum isopropoxide, Grignard reagents such as methylmagnesium iodide, metal hydrides such as sodium hydride, lithium aluminum hydride and the like. The treatment with disodium stilbene usually employed as a solution in an ether such as tetrahydrofuran, for example, has the advantage that it likewise isomerizes the cis-stilbene present to the trans-form. Generally, contacting of the stilbene fraction in conventional vessels adapted for insuring good mixing is all that is required. Any water present must be removed before treating. The amount of the treating agent to be employed will vary with the particular agent employed. In general, amounts of treating agent in the range from about 0.001 to about 0.1% by weight of the stilbene fraction are employed. Temperatures of treatment vary depending upon the agent employed but are usually in the range from about 20° to about 140°C. Separation of the treated stilbene is effected by conventional techniques such as filtration, centrifugation, distillation, decantation and the like.

The polar impurities can also be removed from the stilbene fraction by crystallization. In cases in which the stilbene fraction separated from the reaction effluent is trans-stilbene, crystallization can be effected directly by sufficient cooling, filtration, washing and drying and the recovered trans-stilbene is free of polar impurities. In those cases in which other reaction products such as bibenzyl, cis-stilbene and by-product hydrocarbons such as benzene are present in the stilbene fraction, the fraction may be first fractionated to remove the low-boiling hydrocarbons, then thermally or catalytically isomerized to convert any cis-stilbene to trans-stilbene and thereafter subjected to crystallization to provide trans-stilbene free of polar impurities.

Still another method for removing the polar impurities is extraction of the stilbene from the fraction recovered using suitable solvents.

As previously indicated, the purified stilbene or stilbene fraction can be used to produce styrene by a reverse disproportionation with ethylene. This reaction is preferably conducted in the vapor phase, i.e., the stilbene and ethylene are in the vapor state. The reaction is conducted at a temperature of from about 300°C to about 600°C, preferably at a temperature of from 350°C to 500°C and in the presence of a catalyst. Any catalyst known to be effective for the disproportionation of olefins can be used in this reaction. Suitable olefin disproportionation catalysts are, for example, those which contain or are prepared from materials such as oxides of molybdenum, tungsten, vanadium, niobium, tantalum and rhenium as well as hexacarbonyl compounds and sulfides of tungsten and molybdenum. Those catalysts are generally associated with catalytic carrier materials such as silica, alumina, silica-alumina, magnesia-titania, zironia, thoria, aluminum phosphate and/or zirconium phosphate. The catalytic agents are the reaction products of the mixing, under activating circumstances, of such promoters and such carrier materials. Other inert materials may also be present in the catalyst in subordinate amounts. Thus, the catalysts may also contain subordinate amounts of certain materials, which in some cases exert a favorable effect on the process. Examples of such materials are cobalt oxide and alkaline materials, such as compounds of the alkali- and alkaline earth metals. Some specific examples of suitable catalysts are cobalt molybdate on alumina, and tungsten oxide on silica, alumina or silica-alumina.

The invention is not limited to the use of a specific disproportionation catalyst, but any catalyst, which is suitable for the disproportionation of alkenes, may be used.

The reaction effluent contains, in addition to styrene, unreacted stilbene and ethylene and organic by-products such as ethylbenzene. The styrene can be recovered in any suitable manner. An acceptable method comprises quenching the effluent with cooled styrene to remove the styrene from unreacted stilbene and ethylene and fractionating the styrene to separate and remove ethylbenzene and heavier by-products.

DESCRIPTION OF PREFERRED EMBODIMENTS

The following examples are given as illustrative of the invention and, as such, specifics presented therein are not intended to be considered limitations upon the scope of this invention.

The reactors employed in the following EXAMPLES 1 – 5 are stainless steel tubes one foot long equipped at the upper end with inlet means for introducing the reactant and at the bottom end with outlet means for collecting the reaction effluent or for introducing it into gas chromatograph for analysis.

The reactor employed in the following EXAMPLES 6 – 7 is a two-zone fluidized bed system of 38 mm.-diameter quartz tube 21 inches long equipped at the bottom with inlet means for steam and air, at 8 inches above the bottom with inlet means for toluene, and at the top with outlet means for the reaction effluent. The reaction effluent is cooled to condense the normally liquid and solid products and the remaining gas phase is passed through a wet test meter. Gas chromatography is used to analyze the separated effluent streams.

The reactor employed in the following EXAMPLES 12 – 13 is a one-half inch inside diameter stainless steel tube 30 inches long equipped at one end with reactant inlet means and at the other end with reaction effluent outlet means. The reactor is heated with a radiant furnace. The inlet means is equipped with flow controllers and rotameters. The stilbene is found molten in the inlet means through a differential pressure capillary coil maintained at the temperature of boiling xylene. The outlet means is equipped with means to introduce nitrogen for diluting the reaction effluent and is connected to a gas sampling valve feeding a gas chromatograph.

EXAMPLE 1

Steam and toluene in a 1:1 mole ratio is fed at a temperature of 600°C to the reactor, one-half inch in diameter, heated with a radiant furnace containing 25 ml. of litharge at such a rate to give a one second residence time of the toluene in the reactor. After the reaction has proceeded for four minutes, analysis of the effluent indicates 33.6% of the toluene is reacted of which 68.1% is converted to stilbene, 0.1% to bibenzyl, 20.2% to benzene and 3.9% to $CO_2$.

EXAMPLE 2

Example 1 is repeated except that the temperature is 575°C, the reactor contains a mixture of 25 ml. of litharge and 25 ml. of 140 – 170 mesh alumina having a surface area of <1m$^2$/gm. and the residence time of the toluene is 5 seconds. After 6 minutes of operation and purging the reactor with steam for ten minutes, analysis of the effluent indicates 33% of the toluene is reacted of which 54.8% is converted to stilbene, 2.8% to bibenzyl, 29.3% to benzene, 12.4% to $CO_2$ and 0.7% to coke.

EXAMPLE 3

A magnesia-alumina supported PbO catalyst is prepared by melting 1180.6 grams of $Mg(NO_3)_2 \cdot 6H_2O$ and mixing the melt with 470 grams of 50-150 mesh alumina having a surface area of 250 m$^2$/g. This mixture is calcined at 500°C for 5 hours, screened to remove dust, and calcined at 1100°–1200°C for 12 hours. After cooling this material is screened to provide hard particles (40–270 mesh) of magnesium aluminate spinel having a surface area of 4.3m$^2$/g. These particles are impregnated with sufficient $Pb(NO_3)_2$ to provide a loading of 20% PbO, dried and calcined at 500°C for 4 hours.

Example 1 is repeated except that the steam-toluene mole ratio is 2:1 and the reactor contains 19.7 ml. of the above described supported PbO catalyst. After one minute of operation, analysis of the effluent indicates 41.2% of the toluene is reacted of which 67.1% is converted to stilbene, 1.8% to bibenzyl, 26.8% to benzene and 1.4% to $CO_2$.

EXAMPLE 4

A magnesia-alumina supported PbO catalyst is prepared by forming a solution of 1581 grams of $Al(NO_3)_3 \cdot 9H_2O$ and 541 grams of $Mg(NO_3)_2 \cdot 6H_2O$ in 2 liters of water. The pH of the solution is adjusted to 9.0 by adding ammonium hydroxide to cause precipitation of magnesium and aluminum hydroxides. After filtering, the precipitate is washed with water, dried in vacuo for 16 hours at 120°C, crushed and screened to 20–140 mesh, redried in vacuo for 48 hours at 180°C and calcined at 1200°C for 3.5 hours. After cooling, the calcined precipitate is very hard, has a surface area of 3m$_2$/g. and an XRD analysis of 80–98% magnesium aluminate spinel. The calcined precipate is stirred into a water solution of $Pb(NO_3)_2$ containing sufficient $Pb(NO_3)_2$ to give a loading of 10% PbO. After evaporating the water in vacuo, the mixture is calcined at 600° C for 3.5 hours. The supported catalyst has a surface area of 1.6m$^2$/g.

Example 3 is repeated except that the temperature is 610°C and the residence time of the toluene is 2 seconds. After 1 minute of operation, analysis indicates 30.7% of the toluene is reacted of which 64.4% is converted to stilbene, 6.8% to bibenzyl and 24.8% to benzene.

EXAMPLE 5

The above described reactor, 1 inch in diameter, is loaded with 800 gms. of lead and heated to 600°C. Air is passed through the molten lead until 181 gms. of PbO is formed. Toluene and nitrogen are fed to the reactor at a rate of 1 millimole each per minute for 1 hours. The reaction effluent is analyzed and the results indicate the formation of 39.5 gms. stilbene, 19.3 gms. bibenzyl, 17.2 gms. benzene and 9.3 gms. of $CO_2$ per 100 gms. of toluene reacted, The 181 gms. of PbO is restored by passing air through the molten lead and then 30 ml. of 50–150 mesh alumina having a surface area of 2.5m$^2$/g. is placed in the reactor on top of the lead material. After one hour of operation by feeding toluene and nitrogen at the above noted rate, the reaction effluent is analyzed nd the results indicate the formation of 59.4 g. of stilbene, 2.0 g. of bibenzyl, 19.7 g. of benzene and 12.0 g. of $CO_2$ per 100 g. of toluene reacted.

This example shows that in the presence of alumina the reaction is more selective to stilbene than to bibenzyl.

EXAMPLE 6

A $PbAl_{12}O_{19}$ supported PbO is prepared by impregnating a 50–150 mesh alumina having a surface area of 250 m$^2$/g. with sufficient $Pb(NO_3)_2$ to form $PbAl_{12}O_{19}$ and is then calcined at 1100°C in the presence of air and steam to form the support. This support is then impregnated with sufficient $Pb(NO_3)_2$ to give a loading of 10% PbO. After drying the impregnated support is calcined at 600°C in air.

The reactor is charged with 345 ml. of the above described supported PbO and heated to 595°C. Into the bottom inlet is fed 167 scc/min of air, 94 scc/min of nitrogen and 0.48 ml./min of water. Into the toluene inlet is fed 0.5 ml./min of toluene and 50 scc/min of nitrogen. The residence time of toluene in the reactor is 1.4 seconds. After 149 hours of operation, analysis of the effluent indicates 27.6% of the toluene reacted of which 68.9% is converted to stilbene, 2.0% to bibenzyl, 23.4% to benzene and 3.5% to $CO_2$.

EXAMPLE 7

An alumina-supported PbO is prepared by impregnating a 50–150 mesh alumina having a surface area of 2.6 m$^2$/g, with suffcent $Pb(NO_3)_2$ to provide a loading of 10% of PbO followed by drying and calcination at 700°C in air.

Example 6 is repeated except that 350 ml. of the above described supported PbO is used in the reactor. Analysis of the effluent indicates 33.0% of the toluene is reacted of which 67.9% is converted to stilbene, 4.7% to bibenzyl, 18.6% to benzene and 4.8% to $CO_2$.

EXAMPLE 8

The reactor employed in this example is a two-zone, fluidized-bed system is described above with respect to Examples 6–7 except that the diameter is 7 cm., the length is 100 cm., the toluene inlet means is 35 cm. above the bottom. The reactor is loaded to a depth of 70 cm. with a 50–150 mesh alumina having a surface area of 2.5 m$^2$/g. and a loading of 10% PbO. The feed to the bottom of the reactor is 64 mmol/min. of air and 86 mmol/min. of steam and toluene is fed through the toluene inlet at 18 mmol/min. After condensing the reaction effluent, the normally liquid and solid products are collected and the low boiling materials flashed off through a one foot jacketed column having a bottom temperature of 200°C. The residue is fractionated using a 2.5 cm × 90 cm column filled with an extruded metal packing and the fraction boiling at about 186°C at 20 mm Hg is collected as trans-stilbene.

EXAMPLE 9

The white crystalline solid trans-stilbene obtained in Example 8 is purified of polar organic and inorganic impurities by dissolving the stilbene in toluene and passing the solution at 100°C through a 8 cm × 80 cm bed of 50–100 mesh alumina having a surface area of 250 m$^2$g. After cooling the effluent, the precipitated stilbene is filtered, washed with petroleum ether and drained in vacuo.

EXAMPLE 10

A disproportionation catalyst is prepared by impregnating a pure alumina having a surface area of 250 m$^2$/g. with rhenium hydroxide dissolved in warm, dry dioxane, drying a vacuo and calcining in air at 580°C. Sixteen grams of this catalyst, 2g. of the purified trans-stilbene obtained in Example 9 and 160 ml. of heptane are placed in a 300-ml. stainless steel stirred autoclave. Ethylene is introduced to provide a pressure of 10 psig and the contents are stirred at 1600 RPM for 3 hours at 58°–74°C. Analysis of the products by gas chromatography indicates 27% of the stilbene reacted of which 98% is converted to styrene.

EXAMPLE 11

A 5% $MoO_3$ loading on silica gel disproportionation catalyst is prepared by impregnating 50 gms. of silica gel having a surface area of 350 m$^2$g. with an aqueous solution of 30 g. of $(NH_4)_6Mo_7O_{24}·4H_2O$, drying in vacuo and calcining at 600°C in air. Twenty ml. of this catalyst is charged to a quartz reactor heated by a tube furnace to 570°C. Molten stilbene at 6 cc/hour and ethylene at 6.27 g./hour are fed to the reactor. After 30 minutes of operation, analysis of the condensed effluent product indicates it contains 2.9% styrene.

EXAMPLE 12

A catalyst is prepared by impregnating a 10–14 mesh commercial silica gel with sufficient aqueous solution of potassium hydroxide and ammonium metatungstate to provide a final loading of 0.75% $K_2O$ and 20% $WO_3$ by weight. The impregnated silica gel is dried and calcined in air at 600°C for 4 hours. After calcination, the catalyst is activated by passing hydrogen at a rate of 300 cc./min. at 556°C for 30 minutes over the catalyst followed by passing carbon monoxide at a rate of 300 cc./min. at 575°C for 60 minutes.

Trans-stilbene obtained by Example 9 and ethylene in a 1:5 molar ratio is fed to the above described reactor containing 50 ml. of the catalyst of this example at a rate to provide a 1.24 seconds contact time with the catalyst. The reactor is maintained at 494°C and at 15 psig pressure. Average analysis of the reaction effluent for 6 hours of operation indicates that 73.8% of the stilbene feed is reacted of which 99.1% is converted to styrene.

EXAMPLE 13

A catalyst is prepared by impregnating a 14–30 mesh commercial silica gel with sufficient aqueous solution of ammonium metatungstate to provide a final loading of 20% $WO_3$ by weight. The impregnated silica gel is dried and calcined in air at 600°C for 4 hours.

A commercial trans-stilbene purified by two crystallizations from toluene followed by percolation through silica gel and ethylene in a 1:5 molar ratio is fed to the above described reactor containing 50 ml. of the catalyst of this example at a rate to provide a two-second contact time with the catalyst. The reactor is maintained at 480°C and at ambient pressure. After the reaction has stabilized, analysis of the reaction effluent indicates that 54.9% of the stilbene is reacting of which 92.3% is being converted to styrene.

EXAMPLE 14

Example 13 is repeated except that the ctalyst used in Example 13 is activated by heating at 550°C in CO for 2 hours. After the reaction has stabilized, analysis of the reaction effluent indicates that 75.8% of the stilbene is reacting of which 91.4% is being cnverted to styrene.

EXAMPLE 15

A catalyst support is prepared by four impregnations of alumina with a solution of magnesium nitrate, each impregnation being followed by drying and nitrate decomposition at a temperature of 400°–500°C. The resulting support is calcined at a temperature of 1100°–1200°C until the surface area is 2.5 m$^2$g. This spinel is then impregnated with lead nitrate solution and heated to 400°–500°C to decompose the nitrate and give a loading of 20% PbO.

The catalyst prepared as described above (900 ml) is charged to a stainless steel fixed-bed reactor 85 cm. long and 44.5 mm. in outside diameter. The reactor is operated cyclically by feeding for three minutes a 1:1 molar mixture of toluene and water, purging with steam. reoxidizing lead to lead oxide, purging again with steam and repeating the entire cycle. Contact time is two seconds and reaction temperature is 550°–600°C. Under these conditions, a 33% conversion of toluene is obtained with about 50% selectivity to trans-stilbene.

The reaction effluent is condensed and the water layer separated from the organic layer and discarded. A sample of the organic layer is analyzed and found to contain 1720 parts of polar impurities (calculated as benzophenone) per million parts of trans-stilbene. The organic layer (402g.) is then distilled in a 5-tray Oldershaw column to remove benzene and about 35% of the unreacted toluene. A final bottoms temperature of about 128°C is obtained. The bottoms stream (260g.) is cooled with stirring to 0°C and the resulting slush is filtered to give 86% of wet crystals: The filter cake is washed with 71 g. of chilled toluene yielding 68g. of wet washed crystals analyzing 31% toluene and 69% trans-stilbene. The wet washed crystals contain less than 5 parts of polar impurities (calculated as benzophenone) per million parts of trans-stilbene.

EXAMPLE 16

The cyclic fixed-bed reactor used in Example 15 is charged with 900 ml. of catalyst prepared in essentially the same way as that described in Example 15 and consisting of 15–20% PbO supported on magnesium-aluminate spinel. Toluene and steam in a mole ratio of 1:1 are fed to the reactor maintained at a reaction temperature of 550°–610°C. The reactor is operated cyclically as described in the foregoing example using a residence time of 5 seconds for the reactants in the reactor.

The reaction effluent is introduced into a distillation column where all the water and benzene are removed overhead with some of the toluene while the bottoms temperature is maintained at about 128°C. The bottoms from this distillation column (67g.) containing the stilbene product together with polar impurities, by-products and unreacted toluene before further processing is diluted with an equal volume of xylenes to permit the use of higher temperatures without resorting to pressure in view of the glass equipment being used for experimental purposes. The diluted mixture is intimately contacted with aluminum isopropoxide (0.3 g.) at about 140°C with samples being taken at 5- and 10-minute intervals and analyzed for polar impurities determined as benzophenone. Results of the analyses show a reduction in benzophenone content of about 40% in 5 min., over 80% in 10 min., and removal of substantially all of the original 500 ppm present in 30 min.

EXAMPLE 17

Toluene and steam are reacted in the manner described in Example 15 using a catalyst consisting of PbO on magnesium aluminate spinel. A stilbene fraction (1108 g.) is separated from the reaction effluent which contains 137.5 g. total stilbene. The fraction is added slowly to a vapor saturator comprised of a cylinder equipped with heating means and a distillation head, the temperature being maintained at about 120°C with 20 ml of N$_2$ flowing through the vapor inlet. The collected distillate is principally composed of toluene (89.4%) with a small amount of benzene (9%) and styrene (1.5%). The residue is cooled to 50°C and 150 ml of freshly prepared 0.24N stilbene disodium dissolved in tetrahydrofuran is added and the mixture is agitated for 20 minutes by N$_2$ flow. Distillation is resumed and the saturator temperature gradually increased to 180°C to remove the tetrahydrofuran and additional toluene. The residue is finally stripped with a low nitrogen flow at 200°C for 21 hours. Upon analysis, the residue is found to contain 2.0 % toluene, 1.4% diphenyl, 0.4% diphenylmethane, 13.0% bibenzyl, 80.4% stilbene, 2.2% phenanthrene and minor amounts of other hydrocarbons.

Ethylene is then introduced and bubbled through the molten mass in the saturator now maintained at a temperature of 243°C. Stilbene vapors saturated with ethylene from the saturator are introduced into the reactor described in the previous examples and passed through the bed of catalyst consisting of 4.5% WO$_3$ and 0.07% K$_2$O supported on silica gel of 14–30 mesh size. Average ethylene-to-stilbene molar ratio is 10.7/1, a total amount of 50.7 g. of stilbene are fed during the 6-hour run and 41.6 g. of styrene are produced.

A control run in which the stilbene fraction is topped and stripped in the manner described above but which is not treated with the disodium stilbene produces no measurable styrene.

It will be obvious to persons skilled in the art that various modifications may be made in the invention and process as described in this application. Accordingly, it is intended that all such modifications which reasonably fall within the scope of the appended claims are a part thereof.

What is claimed is:

1. A process for producing stilbene and stilbene derivatives free of polar impurities from toluene and toluene derivatives as the starting hydrocarbon which comprises:
    a. effecting dehydrocoupling of toluene and toluene derivatives in the vapor phase in the presence of a solid metal oxide selected from the group consisting of the oxides of lead, cadmium and bismuth and mixtures thereof at a temperature in the range of from about 500°C to about 650°C, b. separating the dehydrocoupling effluent by distillation to provide a stilbene fraction, c. treating said stilbene fraction to remove polar impurities by either (1) passing it through a bed of an absorbent material capable of adsorbing polar impurities at a temperature in the range of from 75° to 200°C and at such a rate to provide a contact time of the stilbene and absorbent material of from 0.1 second to 15 minutes, or (2) intimately contacting it with a chemical treating agent selected from the group consisting of alkali metals, alkyl aluminums, aluminum alkoxides, Grignard reagents, metal hydrides, phenyllithium and disodium stilbene, or (3) distilling it to remove all compounds boiling below 128°C, and cooling the distillation residue to effect crystallization; and d. recovering said stilbene fraction substantially free of polar impurities.

2. The process of claim 1 wherein the metal oxide is PbO.

3. The process of claim 2 wherein said stilbene fraction is trans-stilbene which is treated by passing it through a bed of activated alumina at a temperature in the range from 125° to 150°C.

4. The process of claim 2 wherein said stilbene fraction is treated by intimately contacting it with a chemical treating agent and said chemical treating agent is aluminum isopropoxide.

5. The process of claim 1 wherein said metal oxide is supported on a solid carrier selected from the group consisting of silica, alumina, silica-alumina and metal silicates.

6. The process of claim 5 wherein the solid carrier is $MgAl_2O_4$ spinel.

7. The process of claim 5 wherein said metal oxide is PbO.

8. The process of claim 6 wherein the metal oxide is PbO.

9. The process of claim 6 wherein the $MgAl_2O_4$ spinel has a surface area of from 0.01 to 10 m²/gram.

10. The process of claim 1 wherein the dehydrocoupling effluent is separated to produce at least three fractions, an unreacted toluene fraction, a cis-stilbene and bibenzyl fraction and a trans-stilbene fraction.

11. The process of claim 10 wherein the unreacted toluene and cis-stilbene and bibenzyl fractions are recycled to the dehydrocoupling reaction.

12. The process of producing styrene from toluene as the starting hydrocarbon which comprises:

a. effecting dehydrocoupling of toluene in the vapor phase in the presence of PbO at a temperature in the range of 500° to 650°C, b. separating the dehydrocoupling effluent by distillation to provide a liquid stilbene fraction, c. treating said stilbene fraction to remove polar impurities therefrom by either (1) passing it through a bed of an adsorbent material capable of adsorbing polar impurities at a temperature in the range of from 75° to 200°C and at such a rate to provide a contact time of the stilbene and adsorbent material of from 0.1 second to 15 minutes, or (2) intimately contacting it with a chemical treating agent selected from the group consisting of alkali metals, alkyl aluminums, aluminum alkoxides, Grignard reagents, metal hydrides, phenyllithium and disodium stilbene, or (3) distilling it to remove all compounds boiling below 128°C, and cooling the distillation residue to effect crystallization;

d. recovering said stilbene fraction substantially free of polar impurities, e. effecting reaction of said recovered stilbene fraction in the vapor phase with ethylene in the presence of a disproportionation catalyst at a temperature in the range from 350° to 500°C, and f. separating and recovering styrene from the catalytic reaction.

13. The process of claim 12 wherein said stilbene fraction is trans-stilbene which is treated by passing it through a bed of activated alumina at a temperature in the range from 125° to 150°C.

14. The process of claim 12 wherein said stilbene fraction is treated by intimately contacting it with a chemical treating agent and said chemical treating agent is aluminum isopropoxide.

15. The process of claim 12 wherein said stilbene fraction is treated by contacting it with a chemical treating agent and said chemical treating agent is disodium stilbene dissolved in tetrahydrofuran.

16. The process of claim 12 wherein said disproportionation catalyst is $WO_3$ on $SiO_2$.

17. The process of claim 12 wherein the PbO is supported on a solid carrier selected from the group consisting of silica, alumina, silica-alumina and metal silicates.

18. The process of claim 17 wherein the solid carrier is $MgAl_2O_4$ spinel.

19. The process of claim 18 wherein the spinel has a surface area of from 0.01 to 10 m²/gram.

20. The process of claim 12 wherein the dehydrocoupling effluent is separated by distillation to produce at least three fractions, a benzene fraction, an unreacted toluene -cis-stilbene - bibenzyl containing fraction, and a trans-stilbene fraction.

21. The process of claim 18 wherein the unreacted toluene and cis-stilbene and bibenzyl are recycled to the dehydrocoupling step.

22. The process of claim 21 wherein the cis-stilbene fraction is isomerized to trans-stilbene and is then passed through the absorbent bed.

23. The process of claim 2 wherein said stilbene fraction is treated by intimately contacting it with a chemical treating agent and said chemical treating agent is disodium stilbene dissolved in tetrahydrofuran.

* * * * *

UNITED STATES PATENT OFFICE
CERTIFICATE OF CORRECTION

Patent No. 3,965,206                    Dated June 22, 1976

Inventor(s) Phillip D. Montgomery et al.

It is certified that error appears in the above-identified patent and that said Letters Patent are hereby corrected as shown below:

In Column 6, line 3, Example 1, for

"0.1% to bibenzyl" read ---9.1% to bibenzyl---.

Signed and Sealed this

Twenty-third Day of May 1978

[SEAL]

Attest:

RUTH C. MASON
Attesting Officer

LUTRELLE F. PARKER
Acting Commissioner of Patents and Trademarks